United States Patent [19]

Gowers et al.

[11] 4,399,129

[45] Aug. 16, 1983

[54] TREATING SHOCK

[75] Inventors: Elizabeth Gowers, Reading; Martin H. Todd, Maidenhead, both of England

[73] Assignee: John Wyeth and Brother Limited, Maidenhead, England

[21] Appl. No.: 343,627

[22] Filed: Jan. 28, 1982

[30] Foreign Application Priority Data

Feb. 12, 1981 [GB] United Kingdom ................. 8104409

[51] Int. Cl.³ ............................................. A61K 31/33
[52] U.S. Cl. .................................................... 424/244
[58] Field of Search .......................................... 424/244

[56] References Cited

U.S. PATENT DOCUMENTS 4,267,182  5/1981  Holsday ............................. 424/260

OTHER PUBLICATIONS

Lancet, Sep. 17 (1980), p. 690.
Chem. Abst. 76-80930k, (1972).

Primary Examiner—Stanley J. Friedman
Attorney, Agent, or Firm—George Tarnowski

[57] ABSTRACT

Meptazinol and its pharmaceutically acceptable acid addition salts can be used in treating shock in mammals.

3 Claims, No Drawings

TREATING SHOCK

This invention relates to a method of treating shock in mammals.

In humans clinical shock is normally characterised by a subnormal temperature, a fall of blood pressure, a feeble rapid pulse, pallor, a cold moist skin, often vomiting, restlessness and anxiety. One of the main characteristics of clinical shock such as that resulting from haemorrhage, trauma and infection in man and other warm blooded mammals is the low blood pressure. However, the use of conventional vasopressor agents to increase the blood pressure may not always be beneficial since the administration of such agents can result in the blood flow in essential organs being reduced. Shock may also be accompanied by considerable pain (e.g. as in shock accompanying trauma). In the past morphine and its opiate analogues have been commonly used to combat the pain. However, morphine may cause further lowering of the blood pressure and therefore any hypotension resulting from the shocked condition may be exacerbated by the administration of the analgesic.

Naloxone had been suggested as an agent to raise the blood pressure in cases of shock (see, for example, M. Tiengo, The Lancet, September 27 1980, p 690). Naloxone is an opiate antagonist and is of no value as an analgesic and, more importantly, its administration will reverse all the analgesic effects of morphine-like analgesic agents. Hence the use of naloxone as an agent for alleviating the hypotensive effects of shock is limited to those cases where opiate analgesia is not required.

U.S. Pat. No. 4,267,182 describes in detail the use of naloxone for treating shock in animals and suggests that it would be possible to use other narcotic antagonists, particularly naltrexone, nalorphine, diprenorphine, levallorphan, pentazocine, metazocine, cyclazocine, etazocine and the pharmaceutically acceptable acid addition salts thereof. Many of these narcotic antagonists suffer from the disadvantages of naloxone mentioned above.

We have now found that meptazinol and its pharmaceutically acceptable salts are useful in treating shock in mammals. Meptazinol is an example of an analgesic having partial opiate antagonistic properties and it does not suffer from the aforementioned disadvantages of pure narcotic antagonists such as naloxone. In addition we have found that meptazinol has a combination of other properties (e.g. activity, lack of side effects, variety of shock situations in which it is active) which make it and its pharmaceutically acceptable salts superior to the narcotic antagonists mentioned in U.S. Pat. No. 4,267,182.

Accordingly the present invention provides a method of treating shock in mammals which comprises administering to a mammal suffering from shock an effective amount of meptazinol or a pharmaceutically acceptable acid addition salt thereof.

In particular, the invention provides a method of relieving the hypotension associated with shock in mammals which comprises administering to a mammal suffering from shock an effective amount of meptazinol or a pharmaceutically acceptable acid addition salt thereof.

In another aspect the invention provides meptazinol or a pharmaceutically acceptable salt thereof for use in the treatment of shock in mammals.

The mammal is preferably man but it can also be, for example, any animal species where treatment of shock is indicated. For example the invention may be used in domestic, farm and laboratory animals, e.g. horses, cattle, dogs, cats and the like.

Examples of acid addition salts which may be used in the invention are those formed from inorganic and organic acids, such as sulphuric, hydrochloric, hydrobromic, phosphoric, tartaric, fumaric, maleic, citric, acetic, formic, methane-sulphonic and p-toluene-sulphonic acids.

In a demonstration of the effectiveness of meptazinol for the treatment of shock, haemorrhagic shock was induced in rats by removal of 20% of the total blood volume. This was accompanied by a modest fall in blood pressure. The effect of the administration of meptazinol, morphine and various narcotic antagonists mentioned in U.S. Pat. No. 4,267,182 on the blood pressure and the heart rate was then determined in groups of five animals [(a) control, morphine treated, meptazinol treated, naloxone treated and pentazocine treated and (b) control, nalorphine treated and diprenorphine treated]. Equianalgesic doses of the meptazinol, morphine and pentazocine were chosen (i.e. those required to produce 80% of maximum analgesia by the intramuscular route). Naloxone was administered at 1 and 10 mg/kg and the doses of nalorphine and diprenorphine chosen were equipotent to 10 mg/kg naloxone. The results are summarised in the following Tables I and II:

TABLE I

Response of Blood Pressure to drug administration following 20% acute haemorrhage in conscious normotensive rats (n = 5)

| | Mean Arterial Pressure (mm Hg) | | | | | |
|---|---|---|---|---|---|---|
| | Pre-drug | | Post-drug | | | |
| | Control | 20m After Haemorrhage | Time After Treatment | | | |
| Treatment | | | 5m | 15m | 30m | 60m |
| (a) | | | | | | |
| Placebo | 133 | 112 | 114 | 122 | 122 | 121 |
| | ± 4.08 | ± 6.07 | ± 4.85 | ± 4.32 | ± 4.18 | ± 3.81 |
| Meptazinol | 142 | 117 | 149** | 153** | 152** | 150** |
| (17.4mg/kg) | ± 7.70 | ± 10.2 | ± 8.15 | ± 4.75 | ± 6.70 | ± 6.32 |
| Pentazocine | 121 | 84 | 117** | 124** | 124** | 124** |
| (10.2mg/kg) | ± 4.12 | ± 14.4 | ± 2.06 | ± 0.58 | ± 0.86 | ± 1.80 |
| Morphine | 125 | 101 | 91.4 | 115* | 121* | 122* |
| (3.4mg/kg) | ± 3.84 | ± 8.47 | ± 7.13 | ± 6.98 | ± 6.38 | ± 3.64 |
| Naloxone | 128 | 99.4 | 108 | 117* | 119* | 115* |
| (10mg/kg) | ± 4.64 | ± 6.84 | ± 4.64 | ± 7.59 | ± 7.40 | ± 8.98 |
| Naloxone | 123 | 106 | 114 | 112 | 112 | 104 |
| (1mg/kg) | ± 5.90 | ± 6.72 | ± 4.13 | ± 4.91 | ± 5.40 | ± 10.2 |
| (b) | | | | | | |
| Placebo | 119 | 86.4 | 103* | 98.8* | 102* | 98.2* |

TABLE I-continued

Response of Blood Pressure to drug administration following 20% acute haemorrhage in conscious normotensive rats (n = 5)

| | Mean Arterial Pressure (mm Hg) | | | | | |
|---|---|---|---|---|---|---|
| | Pre-drug | | Post-drug | | | |
| | Control | 20m After Haemorrhage | Time After Treatment | | | |
| Treatment | | | 5m | 15m | 30m | 60m |
| | ± 5.74 | ± 8.38 | ± 10.2 | ± 8.48 | ± 6.01 | ± 7.71 |
| Nalorphine | 127 | 85.2 | 118** | 121** | 119** | 116** |
| (1mg/kg) | ± 3.68 | ± 10.1 | ± 6.01 | ± 6.09 | ± 5.70 | ± 5.71 |
| Nalorphine | 121 | 70.0 | 120** | 120** | 121** | 110** |
| (10mg/kg) | ± 4.28 | ± 14.4 | ± 3.08 | ± 3.14 | ± 2.18 | ± 2.54 |
| Diprenorphine | 122 | 82.4 | 111* | 107** | 105** | 105** |
| (1mg/kg) | ± 5.01 | ± 9.93 | ± 4.15 | ± 5.70 | ± 5.47 | ± 6.49 |

Haemorrhage caused a significant (P > 0.01) fall in mean arterial pressure in all cases.
The columns headed 'Time After Treatment' show absolute values for mean arterial pressure in mmHg (± S.E.M.) for each group. Statistical analysis was made within the group with respect to post haemorrhage values and is shown as follows: *p < 0.05; **p < 0.001.

TABLE II

Response of heart rate to drug administration following 40% acute haemorrhage in conscious normotensive rats (n = 5)

| | Heart rate (beats per minute) | | | | | |
|---|---|---|---|---|---|---|
| | Pre-drug | | Post-drug | | | |
| | Control | 20m After Haemorrhage | Time After Treatment | | | |
| Treatment | | | 5m | 15m | 30m | 60m |
| (a) | | | | | | |
| Placebo | 402 | 413 | 417 | 433 | 426 | 426 |
| | ± 10.8 | ± 23.3 | ± 28.0 | ± 20.5 | ± 17.4 | ± 19.8 |
| Meptazinol | 437 | 403 | 379 | 432 | 412 | 413 |
| (17.4mg/kg) | ± 14.6 | ± 34.4 | ± 21.2 | ± 22.0 | ± 19.1 | ± 21.3 |
| Pentazocine | 385 | 372 | 401 | 462 | 458 | 470 |
| (10.2mg/kg) | ± 15.8 | ± 44.5 | ± 16.7 | ± 9.30 | ± 9.03 | ± 9.75 |
| Morphine | 467 | 421 | 372 | 472 | 490 | 494 |
| (3.4mg/kg) | ± 11.7 | ± 36.2 | ± 31.7 | ± 31.7 | ± 19.5 | ± 12.6 |
| Naloxone | 397 | 348 | 345 | 377 | 382 | 393 |
| (10mg/kg) | ± 29.7 | ± 40.0 | ± 33.5 | ± 40.1 | ± 28.5 | ± 24.0 |
| Naloxone | 403 | 387 | 390 | 401 | 404 | 400 |
| (1mg/kg) | ± 9.43 | ± 14.1 | ± 17.0 | ± 15.5 | ± 15.9 | ± 17.2 |
| (b) | | | | | | |
| Placebo | 415 | 391 | 394 | 400 | 397 | 394 |
| | ± 17.6 | ± 15.4 | ± 16.9 | ± 10.6 | ± 17.2 | ± 1.7 |
| Nalorphine | 411 | 363 | 420 | 433 | 422 | 408 |
| (1mg/kg) | ± 9.27 | ± 19.7 | ± 15.8 | ± 9.30 | ± 8.46 | ± 11.6 |
| Nalorphine | 407 | 354 | 392 | 415 | 409 | 399 |
| (10mg/kg) | ± 9.43 | ± 19.4 | ± 13.6 | ± 9.22 | ± 10.0 | ± 15.0 |
| Diprenorphine | 406 | 376 | 385 | 401 | 390 | 382 |
| (1mg/kg) | ± 12.1 | ± 12.8 | ± 11.4 | ± 20.0 | ± 22.0 | ± 18.9 |

The results in Table I show that meptazinol causes a rapid reversal of the shock-induced hypotension. Pentazocine and nalorphine also produced reversal of the hypotension but, as indicated in Table II, this was accompanied by tachycardia which is clearly an undesirable side effect when treating haemorrhagic shock. In contrast meptazinol had little effect on the heart rate; bradycardia was measured 5 minutes after drug administration and the heart rate returned towards the group mean value during the remainder of the experiment. Naloxone only produced some reversal of the shock in induced hypotension when administered at 10 mg/kg and even then the effects were not as great as those produced by meptazinol. Similarly the effects produced by diprenorphine in reversing the hypotension were considerably less than those produced by meptazinol. Morphine evoked an initial further hypotension instead of the increase in blood pressure produced by meptazinol.

The activity of meptazinol in reversing hypotension in haemmorhagic shock has been confirmed in other experimental shock conditions. For example, the effect in endotoxic shock was determined in a procedure in which E. coli endotoxin at 10 mg/kg was administered to urethane/chloralose anaesthetised rats. This produced a 47 mm Hg fall in mean arterial pressure (M.A.P.). The effects of meptazinol (17 mg/kg), naloxone (10 mg/kg), pentazocine (10 mg/kg) and morphine (3 mg/kg) on the M.A.P. were determined 90 minutes after administration of the endotoxin. The results are summarised in Table III. In this table all values are mean with S.E.M. in brackets. The statistical significance is indicated:

*$p<0.05$ $p<0.01$ *$p<0.001$.

TABLE III

The effect of drugs or vehicle on MAP (mmHg) during endotoxic shock in urethane/chloralose anaesthetised rats.

| Time | Vehicle (1 ml/kg) | Meptazinol (17 mg/kg) | Naloxone (10 mg/kg) | Pentazocine (10 mg/kg) | Morphine (3 mg/kg) |
|---|---|---|---|---|---|
| Predose | 135(3.8) | 123(6.2) | 127(6.2) | 142(5.8) | 127(4.0) |
| 15' | 97.6(18) | 67.1(2.1) | 108(15) | 98.1(14) | 101(11) |
| 30' | 71.7(7.3) | 61.3(7.4) | 82.1(11) | 72.9(9.6) | 75.0(2.4) |
| 45' | 72.5(7.2) | 61.2(7.5) | 83.8(7.9) | 72.9(10) | 74.6(9.6) |
| 60' | 75.0(6.6) | 66.3(7.5) | 80.8(4.3) | 75.0(6.9) | 77.1(11) |
| 75' | 78.3(7.5) | 73.8(8.7) | 82.5(3.1) | 80.0(7.3) | 85.0(8.0) |
| 90' | 76.7(6.9) | 75.4(4.0) | 81.7(3.0) | 79.6(7.9) | 87.1(4.7) |
| Post-dose | | | | | |
| 5' | 80.0(6.8) | 97.4(4.1)*** | 92.5(3.9)** | 83.8(6.8) | 81.7(7.7) |
| 10' | 80.4(7.0) | 97.4(3.6)*** | 93.3(5.1)** | 80.8(5.4) | 74.6(8.2) |
| 15' | 83.9(6.4) | 97.5(4.2)*** | 97.3(4.7)*** | 80.0(5.1) | 75.0(8.7) |
| 20' | 85.9(6.5) | 96.7(4.5)*** | 95.9(6.2)** | 80.4(5.2) | 75.4(11) |
| 25' | 87.1(7.3) | 99.6(3.6)*** | 102(5.1)*** | 80.0(3.9) | 74.6(6.8) |
| 30' | 87.5(7.3) | 101(3.4)*** | 104(4.7)*** | 80.4(5.4) | 77.9(8.6) |

The results in Table III show that meptazinol produced significant increases in mean arterial pressure in endotoxin treated animals. It was also found that these effects were produced without consistently affecting heart rate. Naloxone behaved similarly but neither petazocine nor morphine were active in raising mean arterial pressure during endotoxic shock.

The effects of meptazinol, and other drugs, has also been investigated in rats subjected to anaphylactic shock. Female rats (200-250 g) were sensitised by an injection of ovalbumin (10 μg i.m.) in aluminum hydroxide gel together with 1×10$^{10}$ killed organisms of *Bordetella pertussis* as adjuvant (i.p.). Eight days later rats were anaesthetised with urethane (800 mg/kg) and chloralose (60 mg/kg). Blood pressure was monitored from the left carotid artery and heart rate was derived from a tachograph triggered by the pressure signal. The trachea was intubated, body temperature maintained at 37°±0.5° C. and drugs administered via a cannula in the left jugular vein.

Mepyramine maleate (0.1 mg/kg s.c.) was injected 10 min prior to challenging animals with 0.05 mg/kg ovalbumin.

Meptazinol, pentazocine, naloxone, morphine or saline vehicle was administered 30 min after the ovalbumin challenge and blood pressure and heart rate were monitored for a further 30 min. The effects on the MAP are summarised in Table IV below. In this table all values are mean and the statistical significance is indicated:

$*p<0.05$ $p<0.01$ $*p<0.001$.

TABLE IV

The effects of drugs and vehicle on the mean arterial pressure (mmHg) of rats subjected to anaphylactic shock.

| Time (mins) | Vehicle | Meptazinol (17 mg/kg) | Pentazocine (10 mg/kg) | Naloxone (10 mg/kg) | Morphine (3 mg/kg) |
|---|---|---|---|---|---|
| Pre-ovalbumin | 111(6) | 124(5) | 124(4) | 115(6) | 120(5) |
| Post-ovalbumin | | | | | |
| 5 | 53(6) | 62(5) | 64(4) | 55(4) | 82(11) |
| 10 | 44(7) | 58(6) | 60(8) | 51(5) | 85(11) |
| 15 | 51(11) | 66(6) | 64(10) | 55(4) | 81(5) |
| 20 | 50(8) | 65(5) | 60(5) | 55(4) | 78(1) |
| 25 | 50(5) | 58(4) | 58(3) | 52(3) | 76(1) |
| 30 | 50(5) | 56(5) | 57(2) | 55(5) | 68(4)*** |
| Post-drug | | | | | |
| 5 | 49(6) | 68(8)*** | 81(6)*** | 65(5)** | 77(4)*** |
| 10 | 49(6) | 87(7)*** | 95(4)*** | 68(6)*** | 97(5)*** |
| 15 | 49(7) | 96(5)*** | 91(3)*** | 68(6)*** | 106(8)*** |
| 20 | 50(7) | 93(4)*** | 87(5)*** | 71(8)*** | 102(6)*** |
| 25 | 50(8) | 93(6)*** | 88(5)*** | 70(8)*** | 98(3)*** |
| 30 | 48(7) | 91(6)*** | 88(5)*** | 70(7)*** | 88(5)*** |

The results in Table IV show that meptazinol significantly raised the blood pressure at all time points compared with saline controls when administered to animals subjected to anaphylactic shock. It was also found that these effects were produced without consistently affecting heart rate. Morphine, pentazocine and naloxone also significantly increased mean arterial pressure at all time points. Naloxone was the least effective of these agents in raising pressure. While morphine and pentazocine were effective in this model only meptazinol demonstrated a consistent effect on blood pressure in all three models: haemorrhagic, endotoxic and anaphylactic shock.

In carrying out the method of the invention meptazinol or a pharmaceutically acceptable acid addition salt thereof can be administered alone by preferably it is administered in the form of a pharmaceutical composition comprising the active ingredient in association with a pharmaceutically acceptable carrier. Any suitable carrier known in the art can be used to prepare the pharmaceutical composition. In such a composition the carrier is generally a solid or liquid, or a mixture of a solid and a liquid.

Solid form compositions include powders, granules, tablets, capsules (e.g. hard and soft gelatin capsules) suppositories and pessaries. The solid carrier can be any of the substances used in preparing solid form compositions. For the administration to patients suffering from shock a particularly preferred solid form composition is a freeze dried dissolving dosage form prepared, for example, by the method described in U.K. Patent Specification No. 1,548,022. Alternative preferred compositions for administration to patients suffering from shock are aerosol or liquid form compositions.

Liquid form compositions include, for example, solutions, suspensions, and emulsions. The active ingredient, for example, can be dissolved or suspended in a pharmaceutically acceptable liquid carrier such as water, an organic solvent, a mixture of both or pharmaceutically acceptable oils or fats. The liquid carrier can contain other suitable pharmaceutical additives such as solubilizers, emulsifiers, buffers, preservatives, sweeteners, flavouring agents, suspending agents, thickening agents, colours, viscosity regulators, stabilisers or osmo-regulators. Suitable examples of liquid carriers for oral and parenteral administration include water (particularly containing additives as above e.g. cellulose derivatives, preferably sodium carboxymethyl cellulose solution), alcohols (including monohydric alcohols and polyhydric alcohols, e.g. glycerol and glycols) and their derivatives, and oils (e.g. fractionated coconut oil and arachis oil). For parenteral administration the carrier can also be an oily ester such as ethyl oleate and isopropyl myristate. Sterile liquid carriers are used in sterile liquid form compositions for parenteral administration.

Preferably the liquid pharmaceutical compositions are sterile solutions or suspensions which can be utilised by, for example, intramuscular or subcutaneous injection. Sterile solutions can also be administered intravenously. Particularly preferred are compositions for administration by the intravenous or intramuscular route.

Preferably the pharmaceutical composition is in unit dosage form. In such form, the composition is subdivided in unit dose containing appropriate quantities of the active ingredient; the unit dosage forms can be packaged compositions, for example, packeted powders, vials, ampoules, prefilled syringes, or sachets with attached needles and containing liquids for injection.

The quantity of the active ingredient in a unit dose of composition may be varied or adjusted from 0.5 mg or less to 750 mg or more, according to the particular need and the activity of the active ingredient. For example, the dosage of meptazinol to be administered to humans intravenously or intramuscularly can be within the range 25 to 300 mg, for example 50 to 150 mg.

The pharmaceutical compositions may contain active ingredients in addition to meptazinol or a salt thereof. For example, the composition may contain an antiemetic, antinauseant, sedative or anxiolytic (e.g. cyclizine, prochloroperazine, thiethylperazine, trifluoperazine, chlorpromazine, promazine, temazepam, diazepam, lorazepam or fluphenazine).

A solution of meptazinol (50 mg/ml) for injection for administration to humans can be prepared from the following ingredients:

|  | per ml |
|---|---|
| meptazinol hydrochloride | 57.80 mg |
| anhydrous dextrose BP | 50.00 mg |
| water for injection BP to | 1.00 ml |

The meptazinol hydrochloride is dissolved in a solution of anhydrous dextrose and the volume adjusted. The solution is sterilised by filtration from a $0.2\mu$ membrane filter into sterile vessels. The filtered solution is aseptically filled into sterile, clear neutral glass ampoules, which are flushed with nitrogen and hermetically sealed.

We claim:

1. A method of treating shock in mammals which comprises administering to a mammal suffering from shock an effective amount of meptazinol or a pharmaceutically acceptable salt thereof.

2. A method according to claim 1 wherein the mammal is suffering from haemorrhagic, endotoxic or anaphylactic shock.

3. A method according to claim 1 or claim 2 wherein the compound administered is meptazinol hydrochloride.

* * * * *